(12) United States Patent
Neuba et al.

(10) Patent No.: US 9,402,797 B2
(45) Date of Patent: *Aug. 2, 2016

(54) MULTI-TONAL ONE STEP DYES III

(71) Applicant: Henkel AG & Co. KGaA, Duesseldorf (DE)

(72) Inventors: Constanze Neuba, Grevenbroich (DE); Frank Janssen, Cologne (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/838,293

(22) Filed: Aug. 27, 2015

(65) Prior Publication Data
US 2015/0374602 A1   Dec. 31, 2015

Related U.S. Application Data

(63) Continuation of application No. PCT/EP2014/052011, filed on Feb. 3, 2014.

(30) Foreign Application Priority Data

Feb. 27, 2013   (DE) .......................... 10 2013 203 228

(51) Int. Cl.
  *A61Q 5/10* (2006.01)
  *A61K 8/49* (2006.01)
  *A61K 8/22* (2006.01)
  *A61K 8/34* (2006.01)
  *A61K 8/41* (2006.01)

(52) U.S. Cl.
  CPC ................. *A61K 8/4926* (2013.01); *A61K 8/22* (2013.01); *A61K 8/347* (2013.01); *A61K 8/411* (2013.01); *A61K 8/415* (2013.01); *A61K 8/4913* (2013.01); *A61Q 5/10* (2013.01); *A61K 2800/4324* (2013.01); *A61K 2800/884* (2013.01)

(58) Field of Classification Search
  CPC ......... A61Q 5/10; A61K 8/411; A61K 8/415; A61K 8/347; A61K 8/4913; A61K 8/4926; A61K 2800/4324
  USPC ....................................... 8/405; 132/202, 208
  See application file for complete search history.

(56) References Cited

U.S. PATENT DOCUMENTS

2005/0193501 A1   9/2005   Chan et al.

FOREIGN PATENT DOCUMENTS

| DE | 10037580 A1 * | 8/2000 | ............... A61Q 5/10 |
| WO | 2009/010883 A2 | 1/2009 | |

OTHER PUBLICATIONS

English translation (Apr. 8, 2016) of the Patent No. DE10037580 A1.*
PCT International Search Report (PCT/EP2014/052011) dated Jul. 30, 2014.

* cited by examiner

Primary Examiner — Eisa Elhilo
(74) Attorney, Agent, or Firm — David K. Benson

(57) ABSTRACT

A cosmetic agent (A) is applied to the fibers and is allowed to act for a period of 30 seconds to 30 minutes, after which a cosmetic agent (B) is applied to the keratinic fibers, which continue to be acted on by agent (A). Both agents (A) and (B) are allowed to act for a period of 5 to 45 minutes, after which the agents (A) and (B) are rinsed out. Agent (A) (a1) contains no oxidation dye precursors of the developer type, (a2) contains one or more oxidation dye precursors of the coupler type, (a3) has a pH of 8.0 to 12.0, and agent (B) (b) contains one or more oxidation dye precursors, (b2) contains one or more oxidizing agents, and (b3) has a pH of 8.0 to 12.0.

16 Claims, No Drawings

MULTI-TONAL ONE STEP DYES III

FIELD OF THE INVENTION

The present invention generally relates to a method for treating keratinic fibers, which in one dyeing step allows the hair to be colored, and at the same time produces a multi-tonal coloring with lighter sections ("highlights") or darker sections ("lowlights") (streaks).

BACKGROUND OF THE INVENTION

Over time, and in particular under the effect of external influences such as light or atmospheric pollutants, the natural color and luster or sheen of the hair is lost or changed. For this reason, hair dyes are in widespread use, either in the hairdressing sector or by home application. For long-lasting, intense colorations having appropriate fastness properties, so-called oxidation dyes are used. Such coloring agents customarily contain oxidation dye precursors, so-called developer components and coupler components, which form the actual dyes with one another under the influence of oxidizing agents or atmospheric oxygen. The oxidation dyes are characterized by excellent, long-lasting color results. For temporary colorings, dyeing or tinting agents which contain so-called direct dyes as coloring component are typically used. In addition to the coloration, lightening or blond shading of the inherent hair color is specifically desired by many consumers, since blonde hair color is regarded as attractive and desirable in terms of fashion. In order to lighten or even bleach substrates, the dyes which color the substrate are decolorized, usually oxidatively, using appropriate oxidizing agents such as hydrogen peroxide.

In the dyeing of hair, in particular the dyeing of hair by home application, the problem arises that natural color shadings are completely covered over, so that multi-tonal colorings are difficult to achieve.

To give the hair a natural appearance, it is proposed to partially decolorize dyed hair by the targeted application of oxidizing agents. The hair sections ("streaks") to which the oxidizing agents are applied fade, at least in part, in the process, resulting in a multi-tonal hair color. The oxidizing agent is applied with a brush or an applicator, wherein the hair not to be treated is optionally protected from the decolorizing by using aluminum foil or a so-called "higlighting cap."

Although this type of application solves the problem of achieving the most natural coloring of hair possible, it only allows application of highlights. For lowlights, i.e., darker sections, it is necessary to perform dyeing again. In each case, a time-consuming second decolorizing or dyeing step is required which follows the original dyeing. In particular for home application, it is therefore necessary to initially color all of the hair before highlights or lowlights can be applied by the user. For many consumers, this is perceived to be too time-consuming as well as frustrating, since the essential color-changing step takes place at the beginning and is "corrected" in a second step.

It is therefore desirable to provide a method which allows multi-tonal colorings in a single dyeing step. The aim is that the dyeing of the hair is accompanied by the creation of highlights or lowlights, so that a result is immediately visible after the coloring agent is rinsed out.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

Method for the oxidative dyeing of keratinic fibers, comprising the following steps: applying a cosmetic agent (A) to the fibers; allowing agent (A) to act for a period of 30 seconds to 30 minutes; applying a cosmetic agent (B) to the keratinic fibers, which continue to be acted on by agent (A); allowing both agents (A) and (B) to act for a period of 5 to 45 minutes; rinsing out agents (A) and (B); wherein agent (A) contains no oxidation dye precursors of the developer type; contains one or more oxidation dye precursors of the coupler type; and has a pH of 8.0 to 12.0; agent (B) (b1) contains one or more oxidation dye precursors; (b2) contains one or more oxidizing agents; and (b3) has a pH of 8.0 to 12.0.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now been found that, as a result of partial pretreatment of fiber areas or streaks, these areas or streaks subsequently have a more intense or less intense color. Due to the pre-penetration of individual fiber areas or streaks, the coloring agent applied immediately afterwards gives the hair a multi-tonal color, and the consumer can admire a natural color result with highlights or lowlights directly after the dyeing step.

The subject matter of the present invention in a first embodiment relates to a method for the oxidative dyeing of keratinic fibers, comprising the following steps:
  A) applying a cosmetic agent (A) to the fibers,
  B) allowing agent (A) to act for a period of 30 seconds to 30 minutes,
  C) applying a cosmetic agent (B) to the keratinic fibers, which continue to be acted on by agent (A),
  D) allowing both agents (A) and (B) to act for a period of 5 to 45 minutes,
  E) rinsing out agents (A) and (B),
  wherein
  agent (A)
    (a1) contains no oxidation dye precursors of the developer type,
    (a2) contains one or more oxidation dye precursors of the coupler type, and
    (a3) has a pH of 8.0 to 12.0,
  agent (B)
    (b1) contains one or more oxidation dye precursors,
    (b2) contains one or more oxidizing agents, and
    (b3) has a pH of 8.0 to 12.0.

A cosmetic agent (A) is applied to the fibers in the first step of the method according to the invention. This agent (A), also referred to below as a pretreatment agent or prepenetration agent, is left on the keratinic fibers for a period of 30 seconds to 30 minutes (step B) of the method according to the invention. Methods preferred according to the invention are characterized by rather brief exposure times of the pretreatment agent. Methods particularly preferred according to the invention are wherein agent (A) is allowed to act on the fibers for a period of 30 seconds to 15 minutes, preferably 30 seconds to 10 minutes, and particularly preferably 30 seconds to 5 minutes, in step B).

Particularly preferred methods according to the invention are further characterized by B) allowing agent (A) to act for a period of 2 to 10 minutes at a temperature of 20 to 60° C., preferably 25 to 55° C., more preferably 27 to 50° C., and very particularly preferably 30 to 45° C.

To produce multi-tonal colorings, agent (A) should not be applied evenly to the keratinic fibers. Preferably only individual areas, particularly preferably only individual strands, are acted on by agent (A). Alternatively, the concentration of agent A on individual streaks may be varied. It is also possible for agent (A) to initially act uniformly on all the keratinic fibers, and for individual areas to then be treated again with agent (A). Treating individual areas/strands with agent (A) multiple times is also possible according to the invention.

Particularly preferred methods according to the invention are wherein the application of cosmetic agent (A) to the fibers in step A) takes place only on individual streaks.

The keratinic fibers are not rinsed out or rubbed out following the exposure time of the pretreatment agent. Instead, in step C) of the method according to the invention, a cosmetic agent (B) is applied to the fibers, which continue to be acted on by agent (A). The mixture of agents (A) and (B) which results from the application of agent (B) to the keratinic fibers is allowed to act for a period of 5 to 45 minutes in step D) of the method according to the invention.

Methods preferred according to the invention are characterized by rather brief exposure times of the mixture of agents (A) and (B). Particularly preferred methods according to the invention are wherein agents (A) and (B) are allowed to act for a period of 5 to 30 minutes, preferably 5 to 20 minutes, particularly preferably 5 to 15 minutes, in step D).

The latter-referenced exposure times refer to the mixture of agents (A) and (B). Since agent (A) has already acted in step B) of the method according to the invention, the fibers have an overall longer contact with the ingredients of agent (A) than with those of agent (B). If agent (A) has been applied only to individual streaks or in individual areas, the ingredients of agent (A) have been able to act more intensely in these areas and thus increase or decrease the action of the ingredients of agent (B) in these areas, thus achieving a darker or lighter coloring of these areas.

After rinsing out agents (A) and (B) in step E) of the method according to the invention, the consumer immediately experiences a multi-tonal color result without having to carrying out an additional step.

According to the invention, agent (A) is free of oxidation dye precursors of the developer type (a1) and contains one or more oxidation dye precursors of the coupler type (a2).

According to the invention, agent (A) additionally contains one or more oxidation dye precursors of the coupler type (a2).

Within the scope of oxidative dyeing, coupler components alone do not form significant coloring, but, rather, always require the presence of developer components. It is therefore preferred according to the invention that when at least one coupler component is used, at least one developer component is also used. In the sense of the invention, coupler components allow at least one substitution of a chemical radical of the coupler with the oxidized form of the developer component. A covalent bond thus forms between the coupler component and the developer component.

Coupler components according to the invention are preferably selected as at least one compound from one of the following classes: m-aminophenol, o-aminophenol, m-diaminobenzene, o-diaminobenzene, and/or the derivatives thereof; naphthalene derivatives containing at least one hydroxy group; di- or trihydroxybenzene; pyridine derivatives; pyrimidine derivatives; certain indole derivatives and indoline derivatives; pyrazolone derivatives (1-phenyl-3-methylpyrazol-5-one, for example); morpholine derivatives (6-hydroxybenzomorpholine or 6-aminobenzomorpholine, for example); quinoxaline derivatives (6-methyl-1,2,3,4-tetrahydroquinoxaline, for example), and mixtures of two or more compounds from one or more of these classes.

Preferred m-aminophenol coupler components are selected from at least one compound from the group 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-diethylaminophenol, N-cyclopentyl-3-aminophenol, 1,3-dihydroxy-5-(methylamino)benzene, 3-ethylamino-4-methylphenol, 2,4-dichloro-3-aminophenol, and the physiologically acceptable salts thereof. Preferred m-diaminobenzene coupler components are selected from at least one compound from the group m-phenylenediamine, 2-(2,4-diaminophenoxy)ethanol, 1,3-bis(2,4-diaminophenoxy)propane, 1-methoxy-2-amino-4-(2'-hydroxyethyl amino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2'-hydroxyethyl)aminobenzene, and the physiologically acceptable salts thereof. Preferred o-diaminobenzene coupler components are selected from at least one compound from the group 3,4-diaminobenzoic acid and 2,3-diamino-1-methylbenzene and the physiologically acceptable salts thereof. Preferred naphthalene derivatives containing at least one hydroxy group are selected from at least one compound of the group 1-naphthol, 2-methyl-1-naphthol, 2-hydroxymethyl-1-naphtho 1,2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene, and 2,3-dihydroxynaphthalene. Preferred di- or trihydroxybenzenes and the derivatives thereof are selected from at least one compound of the group resorcinol, resorcinol monomethyl ether, 2-methylresorcinol, 5-methylresorcinol, 2,5-dimethylresorcinol, 2-chlororesorcinol, 4-chlororesorcinol, pyrogallol, and 1,2,4-trihydroxybenzene. Preferred pyridine derivatives are selected from at least one compound of the group 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 3,4-diaminopyridine, 2-(2-methoxyethyl)amino-3-amino-6-methoxypyridine, 2-(4'-methoxyphenyl)amino-3-aminopyridine, and the physiologically acceptable salts thereof. Preferred pyrimidine derivatives are selected from at least one compound of the group 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine, and 4,6-dihydroxy-2-methylpyrimidine and the physiologically acceptable salts thereof. Preferred indole derivatives are selected from at least one compound of the group 4-hydroxyindole, 6-hydroxyindole, and 7-hydroxyindole and the physiologically acceptable salts thereof. Preferred indoline derivatives are selected from at least one compound of the group 4-hydroxyindoline, 6-hydroxyindoline, and 7-hydroxyindoline and the physiologically acceptable salts thereof.

Coupler components particularly preferred according to the invention are selected from among 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethypamino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diamino-phenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl) amino]ethanol, 3-amino-4-(2-methoxyethoxy)-5-methylphenylamine, 1-amino-3-bis(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of these compounds or the physiologically acceptable salts thereof. Resorcinol, 2-methylresorcinol, 5-amino-2-methylphenol, 3-aminophenol, 2-(2,4-diaminophenoxy)ethanol, 1,3-bis(2,4-diaminophenoxy)propane, 1-methoxy-2-amino-4-(2'-hydroxyethylamino)benzene, 2-amino-3-hydroxypyridine, and 1-naphthol and one of the physiologically acceptable salts thereof are very particularly preferred.

The coupler components are preferably used in a quantity of 0.0001 to 0.5% by weight, preferably 0.001 to 0.2% by weight, in each case based on agent (A).

It has been shown that certain oxidation dye precursors of the coupler type in certain quantities are particularly well suited for use in pretreatment agent (A), and whose application results in multi-tonal colorings that are particularly vivid, wash-fast, abrasion-fast, perspiration-resistant, and UV-resistant.

Methods preferred according to the invention are therefore wherein agent (A), as an oxidation dye precursor of the coupler type (a2), contains one or more compounds from the group 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, and/or the physiologically acceptable salts thereof in a total quantity of 0.1 to 3.5% by weight, preferably 0.3 to 2.8% by weight, more preferably 0.4 to 2.1% by weight, and particularly preferably 0.5 to 1.6% by weight, based on the total weight of agent (A).

Further methods preferred according to the invention are wherein agent (A), as an oxidation dye precursor of the coupler type (a2), contains one or more compounds from the group 3-phenylenediamine, 2-(2,4-diaminophenoxy)ethanol, 1,3-bis(2,4-diaminophenoxy)propane, 1-methoxy-2-amino-4-(2-hydroxyethyl amino)benzene, 1,3-bis(2,4-diaminophenyl)propane, 2,6-bis(2'-hydroxyethylamino)-1-methylbenzene, and/or the physiologically acceptable salts thereof in a total quantity of 0.1 to 3.5% by weight, preferably 0.3 to 2.8% by weight, more preferably 0.4 to 2.1% by weight, and particularly preferably 0.5 to 1.6% by weight, based on the total weight of agent (A).

Further methods preferred according to the invention are wherein agent (A), as an oxidation dye precursor of the coupler type (a2), contains one or more compounds from the group resorcinol, 2-methylresorcinol, and/or 4-chlororesorcinol in a total quantity of 0.1 to 3.5% by weight, preferably 0.3 to 2.8% by weight, more preferably 0.4 to 2.1% by weight, and particularly preferably 0.5 to 1.6% by weight, based on the total weight of agent (A).

Further methods preferred according to the invention are wherein agent (A), as an oxidation dye precursor of the coupler type (a2), contains one or more compounds from the group 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, and/or the physiologically acceptable salts thereof in a total quantity of 0.1 to 3.5% by weight, preferably 0.3 to 2.8% by weight, more preferably 0.4 to 2.1% by weight, and particularly preferably 0.5 to 1.6% by weight, based on the total weight of agent (A).

Further methods preferred according to the invention are wherein agent (A), as an oxidation dye precursor of the coupler type (a2), contains at least one of the following combinations: resorcinol/3-aminophenol; 2-methylresorcinol/3-aminophenol; 4-chlororesorcinol/3-aminophenol; resorcinol/5-amino-2-methylphenol; 2-methylresorcinol/5-amino-2-methylphenol; 4-chlororesorcinol/5-amino-2-methylphenol; resorcinol/2-hydroxy-4-aminophenoxyethanol; 2-methylresorcinol/2-hydroxy-4-aminophenoxyethanol; 4-chlororesorcinol/2-hydroxy-4-aminophenoxyethanol; resorcinol/2-amino-3-hydroxypyridine; 2-methylresorcinol/2-amino-3-hydroxypyridine; 4-chlororesorcinol/2-amino-3-hydroxypyridine; resorcinol/3-amino-2-methylamino-6-methoxypyridine; 2-methylresorcinol/3-amino-2-methylamino-6-methoxypyridine; 4-chlororesorcinol/3-amino-2-methylamino-6-methoxypyridine; resorcinol/2,6-dihydroxy-3,4-dimethylpyridine; 2-methylresorcinol/2,6-dihydroxy-3,4-dimethylpyridine, and/or 4-chlororesorcinol/2,6-dihydroxy-3,4-dimethylpyridine and/or the physiologically acceptable salts thereof.

Pretreatment agent (A) has a pH of 8.0 to 12.0 (a3). Preferred methods according to the invention are wherein agent (A) has a pH (a3) of 8.5 to 11.5, preferably 8.8 to 11.0, more preferably 9.0 to 10.8, and particularly preferably 9.2 to 10.5.

In addition to the oxidation dye precursor(s) of the developer type and the oxidation dye precursor(s) of the coupler type, agent (A) used in the method according to the invention may contain further ingredients. In particular alkalizing agents have proven to be particularly suitable here.

Organic alkalizing agents which are usable according to the invention are preferably selected from alkanolamines of primary, secondary, or tertiary amines having a $C_2$-$C_6$ alkyl base body bearing at least one hydroxyl group. Alkanolamines very particularly preferred according to the invention are selected from the group 2-aminoethan-1-ol (monoethanolamine), 2-amino-2-methylpropan-1-ol, and 2-amino-2-methylpropane-1,3-diol. Monoethanolamine is a particularly preferred alkanolamine. Lysine, arginine, and ornithine are suitable basic amino acids. The inorganic alkalizing agents according to the invention are preferably selected from the group sodium hydroxide, potassium hydroxide, calcium hydroxide, barium hydroxide, sodium phosphate, potassium phosphate, sodium silicate, potassium silicate, sodium carbonate, and potassium carbonate.

Methods particularly preferred according to the invention are wherein agent (A) contains one or more alkalizing agents from the group sodium hydroxide, potassium hydroxide, ammonia, monoethanolamine, and 2-amino-2-methylpropanol in a total quantity of 0.3 to 4.5% by weight, preferably 0.5 to 3.5% by weight, more preferably 0.7 to 2.5% by weight, and particularly preferably 0.9 to 1.5% by weight, based on the total weight of agent (A).

A fairly high viscosity of the agent has proven to be advantageous in allowing prepenetration agent (A) to be applied cleanly and limited to certain areas. For this purpose, it is advantageous when the agent is not present as a paste, viscous cream, or thickened gel, but, rather, has sufficient flowability. In addition, the ready-to-apply agent must certainly have rheological properties that allow application to the fibers to be dyed, but at the same time it must prevent the agent from running or flowing out from the site of action during the application period. The agents (A) therefore preferably have a viscosity of 5 to 100 Pas, more preferably 10 to 50 Pa·s, in particular 10 to 20 Pa·s, and particularly preferably 10 to 16 Pa·s (Brookfield, 22° C., spindle #5, 4 rpm).

Another very particularly preferred embodiment is wherein prepenetration agent (A) has a viscosity of 5000 to 12,000 mPa·s, preferably 5500 to 11,000 mPa·s, more preferably 6000 to 10,000 mPa·s, and very particularly preferably 6500 to 9500 mPa·s (Brookfield, 22° C., spindle #5, 4 rpm).

For this purpose, preferred agents (A) contain at least one thickener and/or at least one gel-forming agent. Corresponding methods according to the invention in which agent (A) additionally contains at least one thickener and/or at least one gel-forming agent are preferred according to the invention.

In a further embodiment, particularly preferred prepenetration agents (A) are therefore wherein they contain at least one anionic polymeric thickener. Preferred anionic polymeric thickeners are selected from crosslinked or uncrosslinked copolymers which contain at least two different monomers from the group of acrylic acid, methacrylic acid, the $C_1$-$C_6$ alkyl esters of acrylic acid, and/or the $C_1$-$C_6$ alkyl esters of methacrylic acid.

Copolymers of acrylic acid, methacrylic acid, or the $C_1$-$C_6$ alkyl esters thereof marketed under the INCI name Acrylates Copolymer are particularly preferred anionic copolymers. The combination of methacrylic acid and ethyl acrylate, and optionally crosslinking multifunctional monomers, is particularly preferred. An example of a preferred commercial product for this purpose is Aculyn® 33 or 33A, marketed by Rohm & Haas.

Prepenetration agent (A) may contain one or more anionic polymeric thickeners from the group of xanthans, alginates, carboxyalkyl celluloses, and hyaluronic acids as further preferred thickeners.

Xanthan is an anionic polysaccharide which is composed of the structural components D-glucose, D-mannose, D-glucuronic acid, acetate, and pyruvate, among others, and which is also known under the NCI name Xanthan Gum.

The salts of alginic acid are referred to as alginates (INCI name Algin). Alginates are acidic, carboxy group-containing polysaccharides composed of D-mannuronic acid and D-guluronic acid in different ratios, which are linked by 1-4 glycosidic bonds. The invention encompasses the alkali salts as well as the alkaline earth salts of alginic acids. The use of alginic acid, sodium alginate, potassium alginate, ammonium alginate, and/or calcium alginate in the agents according to the invention has proven to be particularly advantageous.

Carboxyalkyl celluloses are cellulose ethers in which the hydrogen atoms of the hydroxy groups of the cellulose are partially or completely substituted by carboxyalkyl groups. A preferred carboxyalkyl cellulose is carboxymethyl cellulose, which may preferably be used as an anionic polymer in the form of its sodium salt (sodium carboxymethyl cellulose).

The basic structural unit of hyaluronic acid (INCI names Hyaluronic Acid, Sodium Hyaluronate) is an amino disaccharide which is composed of D-glucuronic acid and N-acetyl-glucosamine in a 1-3 glycosidic bond, and which is β-1-4 glycosidically bonded to the next unit. In the course of the studies leading to the present invention, it has been found that sodium and potassium salts of hyaluronic acid have proven to be particularly suitable for producing intensely coloring dye formulations which are optimized with regard to their viscosity.

Another very particularly preferred embodiment is wherein prepenetration agent (A) contains one or more anionic polymeric thickeners from the group of copolymers of acrylic acid and $C_1$-$C_6$ alkyl esters, the copolymers of methacrylic acid and $C_1$-$C_6$ alkyl esters, xanthan, and carboxymethyl cellulose.

The anionic polymeric thickeners may preferably be used in a total quantity of 0.1 to 15% by weight, more preferably 1 to 10% by weight, and in particular 1.5 to 7.5% by weight, wherein the quantities refer to the total weight of prepenetration agent (A).

In order to bring out the natural multi-tonal color result at the end of the method according to the invention in a particularly distinct and striking manner, pretreatment agent (A) on its own is preferably not able to be used as a separate bleaching, lightening, or coloring agent. For this purpose, it is particularly advantageous when the ready-to-apply agents (A) are free of oxidizing agents, in particular free of hydrogen peroxide and/or persulfates.

Methods preferred according to the invention are wherein agent (A) used in step A) contains no hydrogen peroxide.

The term "free of" means that the agents contain no intentionally added compounds from the mentioned groups. However, traces of these compounds may be introduced into the agents as an impurity or accompanying substance via other raw materials. More precisely, "free of" therefore means that the ready-to-apply agents (A), based on their weight, contain less than 1% by weight, preferably less than 0.5% by weight, more preferably less than 0.25% by weight, even more preferably less than 0.1% by weight, and in particular less than 0.01% by weight, of compounds from the mentioned groups.

Methods preferred according to the invention are wherein agent (A) used in step A), based on its weight, contains less than 1% by weight, preferably less than 0.5% by weight, more preferably less than 0.25% by weight, even more preferably less than 0.1% by weight, and in particular less than 0.01% by weight, of hydrogen peroxide.

Further methods preferred according to the invention are wherein agent (A) used in step A), based on its weight, contains less than 1% by weight, preferably less than 0.5% by weight, more preferably less than 0.25% by weight, even more preferably less than 0.1% by weight, and in particular less than 0.01% by weight, of peroxo compounds.

In step C) of the method according to the invention, a cosmetic agent (B) is applied to the keratinic fibers, which continue to be acted on by agent (A). This agent (B) contains one or more oxidation dye precursors (b1) and one or more oxidizing agents (b2), and has a pH of 8.0 to 12.0.

Methods preferred according to the invention are wherein agent (B), as an oxidation dye precursor (b1), contains one or more oxidation dye precursors of the developer type and of the coupler type.

Preferred agents (B) contain at least one oxidation dye precursor of the developer type. Corresponding methods according to the invention in which agent (B), as an oxidation dye precursor (b1), contains one or more oxidation dye precursors of the developer type are preferred according to the invention.

p-Phenylenediamine derivatives are preferred oxidation dye precursors of the developer type. Preferred p-phenylenediamines are selected from one or more compounds of the group p-phenylenediamine, p-toluylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis-(2-hydroxyethyl)-p-phenylenediamine, 4-N,N-bis-(2-hydroxyethy)amino-2-methylaniline, 4-N,N-bis-(2-hydroxyethypamino-2-chloraniline, 2-(2-hydroxyethyl)-p-phenylenediamine, 2-(1,2-dihydroxyethyl)-p-phenylenediamine, 2-fluoro-p-phenylenediamine, 2-isopropyl-p-phenylenediamine, N-(2-hydroxypropyl)-p-phenylenediamine, 2-hydroxymethyl-p-phenylenediamine, N,N-dimethyl-3-methyl-p-phenylenediamine, N-ethyl-N-2-hydroxyethyl-p-phenylenediamine, N-(2,3-dihydroxypropyl)-p-phenylenediamine, N-(4'-aminophenyl)-p-phenylenediamine, N-phenyl-p-phenylenediamine, 2-(2-hydroxyethyloxy)-p-phenylenediamine, 2-methoxymethyl-p-phenylenediamine, 2-(2-acetylaminoethyloxy)-p-phenylenediamine, N-(2-methoxyethyl)-p-phenylenediamine, N-(4-amino-3-methylphenyl)-N-[3-(1H-imidazole-1-yl)propyl]amine, 5,8-diaminobenzo-1,4-dioxane, and the physiologically acceptable salts thereof. p-Phenylenediamine derivatives particularly preferred according to the invention are selected from at least one compound of the group p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazole-1-yl)propyl]amine, 2-methoxymethyl-p-phenylenediamine, and the physiologically acceptable salts thereof. In addition, it may be preferable according to the invention to use, as the developer component, compounds which contain at least two aromatic nuclei which are substituted with amino and/or hydroxyl groups. Preferred binuclear developer components are in particular selected from at least one of the following compounds: N,N'-bis-(2-hydroxyethyl)-N,N'-bis-(4'-aminophenyl)-1,3-diaminopropan-2-ol, N,N'-bis-(2-hydroxyethyl)-N,N'-bis-(4'-aminophenypethylenediamine, N,N'-bis-(4'-aminophenyl)tetramethylenediamine, N,N'-bis-(2-hydroxyethyl)-N,N'-bis-(4'-aminophenyl)-tetramethylenediamine, N,N'-bis-(4-(methylamino)phenyl)tetramethylenediamine, N,N'-diethyl-N,N'-bis-(4'-amino-3'-methylphenyl)ethylenediamine, bis-(2-hydroxy-5-aminophenyl)methane, N,N'-bis-(4'-aminophenyl)-1,4-diazacycloheptane, N,N'-bis-(2-hydroxy-5-aminobenzyl) piperazine, N-(4'-aminophenyl)-p-phenylenediamine, and 1,10-bis-(2',5'-diaminophenyl)-1,4,7,10-tetraoxadecane and the physiologically acceptable salts thereof. Very particularly preferred binuclear developer components are selected from among N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, or one of the physiologically acceptable salts thereof. In addition, it may be preferred according to the invention to use a p-aminophenol derivative or one of the physiologically acceptable salts thereof as the developer component. Preferred p-aminophenols are in particular p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(2-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(2-hydroxyethyl-aminomethyl)phenol, 4-amino-2-(1,2-dihydroxyethyl)phenol, 4-amino-2-fluorophenol, 4-amino-2-chlorophenol, 4-amino-2,6-dichlorophenol, 4-amino-2-(diethylaminomethyl)phenol, and the physiologically acceptable salts thereof. Very particularly preferred compounds are p-aminophenol, 4-amino-3-methylphenol, 4-amino-2-aminomethylphenol, 4-amino-2-(1,2-dihydroxyethyl)phenol, and 4-amino-2-(diethylaminomethyl)phenol. In addition, the developer component may be selected from o-aminophenol and the derivatives thereof, such as 2-amino-4-methylphenol, 2-amino-5-methylphenol, or 2-amino-4-chlorophenol. Furthermore, the developer component may be selected from heterocyclic developer components such as pyrimidine derivatives, pyrazole derivatives, pyrazolopyrimidine derivatives, and pyrazolopyrazole derivatives, and the physiologically acceptable salts thereof. Preferred pyrimidine derivatives are in particular the compounds 2,4,5,6-tetraaminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine, and 2,5,6-triaminopyrimidine. Preferred pyrazole derivatives are in particular the compounds selected from among 4,5-diamino-1-methylpyrazole, 4,5-diamino-1-(2-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-t-butyl-1-methylpyrazole, 4,5-diamino-1-t-butyl-3-methylpyrazole, 4,5-diamino-1-(2-hydroxyethyl)-3-methylpyrazole, 4,5-diamino-1-ethyl-3-methylpyrazole, 4,5-diamino-1-ethyl-3-(4-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2-aminoethyl) amino-1,3-dimethylpyrazole, and the physiologically acceptable salts thereof, but in particular 4,5-diamino-1-(2-hydroxyethyl)pyrazole. Preferred pyrazolopyrimidines are the compounds selected from among pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidine-7-ylamino)ethanol, 2-(7-aminopyrazolo[1,5-a]pyrimidine-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]pyrimidine-3-yl)-(2-hydroxyethypamino]ethanol, 5,6-dimethylpyrazolo [1,5-a] pyrimidine-3,7-diamine, 2, 6-dimethylpyrazolo [1,5-a] pyrimidine-3,7-diamine, 3-amino-7-dimethylamino-2,5-dimethylpyrazolo[1,5-a]pyrimidine, and the physiologically acceptable salts thereof, and the tautomeric forms thereof when a tautomeric equilibrium is present. 2,3-Diamino-6,7-dihydro-1H,5H-pyrazolo[1,2-a]pyrazol-1-one is a preferred pyrazolopyrazole derivative.

Particularly preferred developer components are selected from at least one compound from the group p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diamino-propan-2-ol, bis-(2-hydroxy-5-aminophenyl) methane, 1,3-bis-(2,5-diaminophenoxy)propan-2-ol, N,N'-bis-(4-aminophenyl)-1,4-diazacycloheptane, 1,1-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, and the physiologically acceptable salts thereof. Very particularly preferred developer components are p-toluylenediamine, 2-(2-hydroxyethyl)-p-phenylenediamine, 2-methoxymethyl-p-phenylenediamine, N-(4-amino-3-methylphenyl)-N-[3-(1H-imidazole-1-yl)propyl]amine, and/or 4,5-diamino-1-(2-hydroxyethyl)pyrazole and the physiologically acceptable salts thereof.

It has been shown that certain oxidation dye precursors of the developer type in certain quantities are particularly well suited for use in agent (B) and whose application results in multi-tonal colorings that are particularly vivid, wash-fast, abrasion-fast, perspiration-resistant, and UV-resistant.

Particularly preferred methods according to the invention are wherein agent (B), as an oxidation dye precursor of the developer type, contains one or more compounds from the group p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazole-1-yl)propyl]amine, and/or the physiologically acceptable salts thereof in a total quantity of 0.1 to 3.5% by weight, preferably 0.3 to 2.8% by weight, more preferably 0.4 to 2.1% by weight, and particularly preferably 0.5 to 1.6% by weight, based on the total weight of agent (B).

Further particularly preferred methods according to the invention are wherein agent (B), as an oxidation dye precursor of the developer type, contains one or more compounds from the group bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, and amino-3-methylphenol, and/or the physiologically acceptable salts thereof in a total quantity of 0.1 to 3.5% by weight, preferably 0.3 to 2.8% by weight, more preferably 0.4 to 2.1% by weight, and particularly preferably 0.5 to 1.6% by weight, based on the total weight of agent (B).

Further particularly preferred methods according to the invention are wherein agent (B), as an oxidation dye precursor of the developer type, contains one or more compounds from the group 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo [1,2-a]pyrazol-1-one, and/or the physiologically acceptable salts thereof in a total quantity of 0.1 to 3.5% by weight, preferably 0.3 to 2.8% by weight, more preferably 0.4 to 2.1% by weight, and particularly preferably 0.5 to 1.6% by weight, based on the total weight of agent (B).

Further particularly preferred methods according to the invention are wherein agent (B), as an oxidation dye precursor of the developer type, contains at least one of the following combinations: p-toluylenediamine/2-(2-hydroxyethyl)-p-phenylenediamine; p-toluylenediamine/2-methoxymethyl-p-phenylenediamine; p-toluylenediamine/N,N-bis-(2-hydroxyethyp-p-phenylenediamine; p-toluylenediamine/2-methoxymethyl-p-phenylenediamine; p-toluylenediamine/N-(4-amino-3-methylphenyl)-N-[3-(1H-imidazole-1-yl)propyl]amine; p-toluylenediamine/bis-(2-hydroxy-5-aminophenyl)methane; p-toluylenediamine/4-amino-3-methylphenol and amino-3-methylphenol; p-toluylenediamine/4,5-diamino-1-(2-hydroxyethyl)pyrazole; p-toluylenediamine/2,4,5,6-tetraaminopyrimidine; 2-(2-hydroxyethyp-p-phenylenediamine/2-methoxymethyl-p-phenylenediamine; 2-(2-hydroxyethyl)-p-phenylenediamine/N,N-bis-(2-hydroxyethyl)-p-phenylenediamine; 2-(2-hydroxyethyl)-p-phenylenediamine/2-methoxymethyl-p-phenylenediamine; 2-(2-hydroxyethyl)-p-phenylenediamine/N-4-amino-3-methylphenyl)-N-[3-(1H-imidazole-1-yl)propyl]amine; 2-(2-hydroxyethyl)-p-phenylenediamine/bis-(2-hydroxy-5-aminophenypmethane; 2-(2-hydroxyethyl)-p-phenylenediamine/4-amino-3-methylphenol; 2-(2-hydroxyethyl)-p-phenylenediamine/4,5-diamino-1-(2-hydroxyethyl)pyrazole; 2-(2-hydroxyethyl-p-phenylenediamine/2,4,5,6-tetraaminopyrimidine; 2-methoxymethyl-p-phenylenediamine/2-(2-hydroxyethyl)-p-phenylenediamine; 2-methoxymethyl-p-phenylenediamine/2-methoxymethyl-p-phenylenediamine; 2-methoxymethyl-p-phenylenediamine/N,N-bis-(2-hydroxyethyl)-p-phenylenediamine; 2-methoxymethyl-p-phenylenediamine/2-methoxymethyl-p-phenylenediamine; 2-methoxymethyl-p-phenylenediamine/N-(4-amino-3-methylphenyl)-N-[3-(1H-imidazol-1-yl)propyl]amine; 2-methoxymethyl-p-phenylenediamine/bis-(2-hydroxy-5-aminophenyl)methane; 2-methoxymethyl-p-phenylenediamine/4-amino-3-methylphenol; 2-methoxymethyl-p-phenylenediamine/4,5-diamino-1-(2-hydroxyethyl)pyrazole; 2-methoxymethyl-p-phenylenediamine/2,4,5,6-tetraaminopyrimidine, and/or 4-amino-3-methylphenol and amino-3-methylphenol/4,5-diamino-1-(2-hydroxyethyl)pyrazole, and/or the physiologically acceptable salts thereof.

According to the invention, agent (B) preferably additionally contains one or more oxidation dye precursors of the coupler type.

Suitable preferred oxidation dye precursors of the coupler type have already been described in detail above. The corresponding compounds are also preferably usable in agent (B). It has been shown that certain oxidation dye precursors of the developer type in certain quantities are particularly well suited for use in agent (B), and whose application results in multi-tonal colorings that are particularly vivid, wash-fast, abrasion-fast, perspiration-resistant, and UV-resistant.

Methods preferred according to the invention are therefore wherein agent (B), as an oxidation dye precursor of the coupler type, contains one or more compounds from the group 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl) amino-2-methylphenol, 2,4-dichloro-3-aminophenol, 2-aminophenol, and/or the physiologically acceptable salts thereof in a total quantity of 0.1 to 3.5% by weight, preferably 0.3 to 2.8% by weight, more preferably 0.4 to 2.1% by weight, and particularly preferably 0.5 to 1.6% by weight, based on the total weight of agent (A).

Further methods preferred according to the invention are wherein agent (B), as an oxidation dye precursor of the coupler type, contains one or more compounds from the group 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl) propane, 2,6-bis(2'-hydroxyethylamino)-1-methylbenzene, and/or the physiologically acceptable salts thereof in a total quantity of 0.1 to 3.5% by weight, preferably 0.3 to 2.8% by weight, more preferably 0.4 to 2.1% by weight, and particularly preferably 0.5 to 1.6% by weight, based on the total weight of agent (A).

Further methods preferred according to the invention are wherein agent (B), as an oxidation dye precursor of the coupler type, contains one or more compounds from the group resorcinol, 2-methylresorcinol, and/or 4-chlororesorcinol in a total quantity of 0.1 to 3.5% by weight, preferably 0.3 to 2.8% by weight, more preferably 0.4 to 2.1% by weight, and particularly preferably 0.5 to 1.6% by weight, based on the total weight of agent (A).

Further methods preferred according to the invention are wherein agent (B), as an oxidation dye precursor of the coupler type, contains one or more compounds from the group 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, and/or the physiologically acceptable salts thereof in a total quantity of 0.1 to 3.5% by weight, preferably 0.3 to 2.8% by weight, more preferably 0.4 to 2.1% by weight, and particularly preferably 0.5 to 1.6% by weight, based on the total weight of agent (A).

Further methods preferred according to the invention are wherein agent (B), as an oxidation dye precursor of the coupler type, contains at least one of the following combinations: resorcinol/3-aminophenol; 2-methylresorcinol/3-aminophenol; 4-chlororesorcinol/3-aminophenol; resorcinol/5-amino-2-methylphenol; 2-methylresorcinol/5-amino-2-methylphenol; 4-chlororesorcinol/5-amino-2-methylphenol; resorcinol/2-hydroxy-4-aminophenoxyethanol; 2-methylresorcinol/2-hydroxy-4-aminophenoxyethanol; 4-chlororesorcinol/2-hydroxy-4-aminophenoxyethanol; resorcinol/2-amino-3-hydroxypyridine; 2-methylresorcinol/2-amino-3-hydroxypyridine; 4-chlororesorcinol/2-amino-3-hydroxypyridine; resorcinol/3-amino-2-methylamino-6-methoxypyridine; 2-methylresorcinol/3-amino-2-methylamino-6-methoxypyridine; 4-chlororesorcinol/3-amino-2-methylamino-6-methoxypyridine; resorcinol/2,6-dihydroxy-3,4-dimethylpyridine; 2-methylresorcinol/2,6-dihydroxy-3,4-dimethylpyridine, and/or 4-chlororesorcinol/2,6-dihydroxy-3,4-dimethylpyridine, and/or the physiologically acceptable salts thereof.

As already mentioned, it is possible, if desired, to provide a multi-tonal coloring having shadings of more or less varying intensity which differ from one another with regard to the oxidation dye precursors agents used in agents (A) and (B). For a very natural-looking multi-tonal coloring with smooth transitions, methods according to the invention are preferred in which agents (A) and (B) contain the same oxidation dye precursors of the coupler type.

If greater contrasts are desired which are manifested in a more brilliant multi-tonal appearance of the coloring, methods according to the invention have proven suitable in which agents (A) and (B) contain different oxidation dye precursors of the coupler type.

Agent (B) preferably contains more oxidation dye precursors, based on its weight, than agent (A) contains couplers, based on its weight.

Methods according to the invention in which the quantity ratio of the total quantity of all oxidation dye precursors of coupler type (a2) in agent (A) to the total quantity of all oxidation dye precursors (b1) in agent (B) has a value (a2)/(b1) of 1:1 to 1:10, preferably 1:2 to 1:8, more preferably 1:2 to 1:5, and particularly preferably 1:2 to 1:3, are particularly preferred.

The ready-to-apply agents (B) additionally contain one or more oxidizing agents (b2). Oxidative coloring agents are customarily offered in the form of a kit (multi-component packaging unit) made up of two components, the first component containing the oxidation dye precursors and an alkalizing agent (ammonia, for example), and the second component containing the oxidizing agent. Peroxides, for example hydrogen peroxide, are generally used as the oxidizing agent.

The oxidation dye precursors (developer and coupler) themselves are not colored; rather, the formation of the actual dyes takes place only in the course of the application by contact of the oxidation dye precursors with the oxidizing agent (preferably hydrogen peroxide). In a chemical reaction, the developers (such as p-phenylenediamine derivatives or p-aminophenol derivatives, for example) used as oxidation dye precursors are initially oxidatively converted, using hydrogen peroxide, into a reactive intermediate stage, also referred to as quinoneimine or quinonediimine, which then reacts with the couplers in an oxidative coupling reaction to form the particular dye.

All of the above statements concerning agent (B) refer to the ready-to-apply mixture, even if it has been obtained from multiple preparations (B1), (B2), and so forth, by mixing only immediately prior to application.

Persulfates, peroxodisulfates, chlorites, hypochlorites, and in particular hydrogen peroxide and/or one of its solid addition products with organic or inorganic compounds is/are suitable as the oxidizing agent.

To prevent an undesirable premature reaction of the oxidation dye precursors due to the oxidizing agent, it is practical to package the oxidation dye precursors and the oxidizing agent itself separate from one another, and to bring them into contact only immediately prior to application.

In a further embodiment of the present invention, agents (B) are therefore preferred which are wherein they are produced immediately prior to application by mixing at least two preparations, wherein the at least two preparations are provided in at least two separately packaged containers, and one container contains a coloring agent (B1) which contains at least one oxidation dye precursor in a cosmetic carrier, and another container contains an oxidizing agent preparation (B2) which contains at least one oxidizing agent.

The oxidizing agent preparation (B2) preferably contains hydrogen peroxide and/or one of its solid addition products with organic or inorganic compounds, such as urea, melamine, and sodium borate, as the oxidizing agent.

Such oxidizing agent preparations (B2) are preferably aqueous, flowable oxidizing agent preparations. Preferred preparations (B2) are wherein the flowable oxidizing agent preparation (B2), based on its weight, contains 40 to 90% by weight, preferably 50 to 85% by weight, particularly preferably 55 to 80% by weight, more preferably 60 to 77.5% by weight, and in particular 65 to 75% by weight, of water.

The quantity of oxidizing agent in the ready-to-apply agent (B) is preferably 0.5 to 12% by weight, more preferably 2 to 10% by weight, particularly preferably up to 3 to 6% by weight (calculated as 100% $H_2O_2$), in each case based on the ready-to-apply agent (B).

In another preferred embodiment, agent (B) is an agent for dyeing, and optionally at the same time for lightening, keratinic fibers, which preferably contains 0.5 to 15% by weight, more preferably 1 to 12.5% by weight, particularly preferably 1.5 to 10% by weight, and in particular 2 to 6% by weight, of hydrogen peroxide, in each case based on the total weight of the ready-to-apply agent (B).

However, according to the invention, the oxidation dye may also be applied to the hair together with a catalyst which activates the oxidation of the dye precursors. Such catalysts are, for example, certain enzymes, iodides, quinones, or metal ions.

It has proven to be advantageous when the oxidizing agent preparations (B2) according to the invention additionally contain at least one stabilizer or complexing agent for stabilizing the hydrogen peroxide. Particularly preferred stabilizers are in particular EDTA and EDDS, and phosphonates, in particular 1-hydroxyethane-1,1-diphosphonate (HEDP) and/or ethylenediamine tetramethylene phosphonate (EDTMP) and/or diethylenetriamine pentamethylene phosphonate (DTPMP) or the sodium salts thereof.

To achieve an enhanced lightening and bleaching action, agent (B) may additionally contain at least one peroxo salt. Suitable peroxo salts are inorganic peroxo compounds, preferably selected from the group comprising ammonium peroxodisulfate, alkali metal peroxodisulfates, ammonium peroxomonosulfate, alkali metal peroxomonosulfates, alkali metal peroxodiphosphates, and alkaline earth metal peroxides. Peroxodisulfates are particularly preferred, in particular ammonium peroxodisulfate, potassium peroxodisulfate, and sodium peroxodisulfate.

The persulfates are contained in agent (B) in each case in a quantity of 0.5 to 20% by weight, preferably 1 to 12.5% by weight, particularly preferably 2.5 to 10% by weight, and in particular 3 to 6% by weight, based on the total weight of the ready-to-apply agent.

Agent (B) may also contain an alkalizing agent; it has proven to be particularly preferred when agent (B) has a lower pH than does agent (A). Corresponding methods according to the invention in which agent (A) has a higher pH than does agent (B) are preferred due to the higher resistances of the colorings.

The ready-to-apply coloring agents (B) may also contain additional active substances, auxiliary substances, and additives to improve the coloring power and to adjust further desired properties of the agents.

The ready-to-apply coloring agents are preferably provided as a liquid preparation, and therefore a surface-active substance is additionally added to the agents, such surface-active substances being referred to as surfactants or as emulsifiers, depending on the field of application. They are preferably selected from anionic, cationic, zwitterionic, amphoteric, and nonionic surfactants and emulsifiers.

Agents which are preferred according to the invention are wherein the agent additionally contains at least one anionic surfactant. Preferred anionic surfactants are fatty acids, alkyl sulfates, alkyl ether sulfates, and ether carboxylic acids containing 10 to 20 C atoms in the alkyl group and up to 16 glycol ether groups in the molecule. The anionic surfactants are used in proportions of 0.1 to 45% by weight, preferably 1 to 30% by weight, and very particularly preferably 1 to 15% by weight, based on the total quantity of the ready-to-apply agent.

Agents which are preferred according to the invention are wherein the agent additionally contains at least one zwitterionic surfactant. Preferred zwitterionic surfactants are betaines, N-alkyl-N,N-dimethylammonium glycinates, N-acylaminopropyl-N,N-dimethylammonium glycinates, and 2-alkyl-3-carboxymethyl-3-hydroxyethyl imidazolines. One preferred zwitterionic surfactant is known under the INCI name Cocamidopropyl Betaine.

Agents which are preferred according to the invention are wherein the agent additionally contains at least one amphoteric surfactant. Preferred amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids. Particularly preferred amphoteric surfactants are N-cocoalkylaminopropionate, cocoacylaminoethylaminopropionate, and $C_{12}$-$C_{18}$ acyl sarcosine.

In addition, it has proven to be advantageous when the agents contain further nonionogenic surface-active substances. Examples of preferred nonionic surfactants are alkylene oxide addition products with fatty alcohols and fatty acids, in each case containing 2 to 30 mol ethylene oxide per mol of fatty alcohol or fatty acid. Preparations having excellent properties are likewise obtained when they contain fatty acid esters of ethoxylated glycerin as nonionic surfactants.

The nonionic, zwitterionic, or amphoteric surfactants are used in proportions of 0.1 to 45% by weight, preferably 1 to 30% by weight, and very particularly preferably 1 to 15% by weight, based on the total quantity of the ready-to-apply agents.

The ready-to-apply coloring agents may contain further auxiliary substances and additives. Thus, it has proven to be advantageous when the agents contain at least one thickener. In principle, there are no limitations with regard to these thickeners. Organic as well as strictly inorganic thickeners may be used.

Suitable thickeners are anionic synthetic polymers; cationic synthetic polymers; naturally occurring thickeners, such as nonionic guar gums, scleroglucan gums, or xanthan gums, gum arabic, gum ghatti, karaya gum, gum tragacanth, carrageenan gum, agar-agar, locust bean gum, pectins, alginates, starch fractions, and derivatives such as amylose, amylopectin, and dextrins, and cellulose derivatives such as methylcellulose, carboxyalkyl celluloses, and hydroxyalkyl celluloses; nonionic synthetic polymers such as polyvinyl alcohol or polyvinylpyrrolidinone; and inorganic thickeners, in particular phyllosilicates such as bentonite, in particular smectites such as montmorillonite or hectorite.

Zwitterionic polymers may also be contained in the agents according to the invention.

Preferred zwitterionic polymers are selected from the group of
  copolymers of dimethyldiallylammonium salts and acrylic acid, for example Polyquaternium-22,
  copolymers of dimethyldiallylammonium salts and methacrylic acid,
  copolymers of N,N,N-trimethyl-3-[(2-methyl-1-oxo-2-propen-1-yl)amino]-1-propanaminium salts and acrylic acid,
  copolymers of N,N,N-trimethyl-3-[(2-methyl-1-oxo-2-prop en-1-yl)amino]-1-propanaminium salts and methacrylic acid,
  copolymers of N,N,N-trimethyl-2-[(2-methyl-1-oxo-2-propen-1-yl)amino]-1-ethanaminium salts and acrylic acid, copolymers of N,N,N-trimethyl-2-[(2-methyl-1-oxo-2-propen-1-yl)amino]-1-ethanaminium salts and methacrylic acid, copolymers of N,N,N-trimethyl-3-[(2-methyl-1-oxo-2-propen-1-yl)amino]-1-propanaminium salts, acrylic acid, and acrylamide, for example Polyquaternium-53, copolymers of N,N,N-trimethyl-3-[(2-methyl-1-oxo-2-propen-1-yl)amino]-1-propanaminium salts, methacrylic acid, and acrylamide, copolymers of 1-ethenyl-3-methyl-1H-imidazolium salts, 1-ethenyl-1H-imidazole, 1-ethenyl-2-pyrrolidinone, and methacrylic acid, for example Polyquaternium-86, copolymers of 1-ethenyl-3-methyl-1H-imidazolium salts, 1-ethenyl-1H-imidazole, 1-ethenyl-2-pyrrolidinone, and acrylic acid.

Mixtures of the above-mentioned preferred zwitterionic polymers (c) may also be contained in the agents according to the invention.

In addition, it has been shown that the stated object according to the invention may in particular be achieved completely and satisfactorily when the agents used in the method according to the invention contain further selected formulation components.

It has thus been found that the additional presence of certain higher-chain fatty alcohols further improves the color result of the compositions according to the invention. It is therefore preferred when the agents used in the method according to the invention additionally contain one or more fatty alcohols from the group arachidyl alcohol (eicosan-1-ol), gadoleic alcohol ((9Z)-eicos-9-en-1-01), arachidonic alcohol ((5Z,8Z,11Z,14Z)-eicosa-5,8,11,14-tetraen-1-ol), heneicosyl alcohol (heneicos an-1-ol), behenyl alcohol (docosan-1-ol), erucyl alcohol ((13Z)-docos-13-en-1-ol), and brassidyl alcohol ((13E)-docosen-1-ol).

Particularly suitable agents contain one or more higher-chain alcohols of the above-mentioned group in a total quantity of 1.0 to 10.0% by weight, preferably 1.4 to 8.0% by weight, more preferably 1.8 to 6.0% by weight, and particularly preferably 2.0 to 4.0% by weight, based on the total weight of the ready-to-apply agent.

In another preferred embodiment, an agent used in the method according to the invention is therefore wherein it additionally contains one or more fatty alcohols from the group arachidyl alcohol (eicosan-1-ol), gadoleic alcohol ((9Z)-eicos-9-en-1-ol), arachidonic alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and brassidyl alcohol ((13E)-docosen-1-ol) in a total quantity of 0.1 to 10.0% by weight, preferably 1.4 to 8.0% by weight, more preferably 1.8 to 6.0% by weight, and particularly preferably 2.0 to 4.0% by weight, based on the total weight of the ready-to-apply agent.

It has been shown that a pretreatment at slightly elevated temperatures can make the multi-tonal effects even more vivid. Methods preferred according to the invention are wherein agent (A) is allowed to act at a temperature of at least 40° C. in step B).

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. Method for the oxidative dyeing of keratinic fibers, comprising the following steps:
   A) applying a cosmetic agent (A) to the fibers,
   B) allowing agent (A) to act for a period of 30 seconds to 30 minutes,
   C) applying a cosmetic agent (B) to the keratinic fibers, which continue to be acted on by agent (A),
   D) allowing both agents (A) and (B) to act for a period of 5 to 45 minutes,
   E) rinsing out agents (A) and (B), wherein
   agent (A)
      (a1) contains no oxidation dye precursors of the developer type,
      (a2) contains one or more oxidation dye precursors of the coupler type, and
      (a3) has a pH of 8.0 to 12.0,
   agent (B)
      (b1) contains one or more oxidation dye precursors,
      (b2) contains one or more oxidizing agents, and
      (b3) has a pH of 8.0 to 12.0.

2. Method according to claim 1, wherein agent (A), as an oxidation dye precursor of the coupler type (a2), contains one or more compounds selected from the group consisting of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, and the physiologically acceptable salts thereof in a total quantity of 0.1 to 3.5% by weight based on the total weight of agent (A).

3. Method according to claim 1, wherein agent (A), as an oxidation dye precursor of the coupler type (a2), contains one or more compounds selected from the group consisting of 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, and the physiologically acceptable salts thereof in a total quantity of 0.1 to 3.5% by weight based on the total weight of agent (A).

4. Method according to claim 1, wherein agent (A), as an oxidation dye precursor of the coupler type (a2), contains one or more compounds selected from the group consisting of resorcinol, 2-methylresorcinol, and 4-chlororesorcinol in a total quantity of 0.1 to 3.5% by weight based on the total weight of agent (A).

5. Method according to claim 1, wherein agent (A), as an oxidation dye precursor of the coupler type (a2), contains one or more compounds selected from the group consisting of 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, and the physiologically acceptable salts thereof in a total quantity of 0.1 to 3.5% by weight based on the total weight of agent (A).

6. Method according to claim 1, wherein agent (A), as an oxidation dye precursor of the coupler type (a2), contains at least one combination selected from the group consisting of: resorcinol/3-aminophenol; 2-methylresorcinol/3-aminophenol; 4-chlororesorcinol/3-aminophenol; resorcinol/5-amino-2-methylphenol; 2-methylresorcinol/5-amino-2-methylphenol; 4-chlororesorcinol/5-amino-2-methylphenol;

resorcinol/2-hydroxy-4-aminophenoxyethanol; 2-methylresorcinol/2-hydroxy-4-aminophenoxyethanol; 4-chlororesorcinol/2-hydroxy-4-aminophenoxyethanol; resorcinol/2-amino-3-hydroxypyridine; 2-methylresorcinol/2-amino-3-hydroxypyridine; 4-chlororesorcinol/2-amino-3-hydroxypyridine; resorcinol/3-amino-2-methylamino-6-methoxypyridine; 2-methylresorcinol/3-amino-2-methylamino-6-methoxypyridine; 4-chlororesorcinol/3-amino-2-methylamino-6-methoxypyridine; resorcinol/2,6-dihydroxy-3,4-dimethylpyridine; 2-methylresorcinol/2,6-dihydroxy-3,4-dimethylpyridine, 4-chlororesorcinol/2,6-dihydroxy-3,4-dimethylpyridine, and the physiologically acceptable salts thereof.

7. Method according to claim 1, wherein agent (A) has a pH (a3) of 8.5 to 11.5.

8. Method according to claim 1, wherein agent (A) additionally contains one or more alkalizing agents selected from the group consisting of sodium hydroxide, potassium hydroxide, ammonia, monoethanolamine, and 2-amino-2-methylpropanol in a total quantity of 0.3 to 4.5% by weight based on the total weight of agent (A).

9. Method according to claim 1, wherein agent (A) is allowed to act on the fibers for a period of 30 seconds to 15 minutes in step B).

10. Method according to claim 1, wherein agent (A) additionally contains at least one thickener and/or at least one gel-forming agent.

11. Method according to claim 1, wherein agent (B) contains one or more oxidation dye precursors of the developer type and of the coupler type as oxidation dye precursor (b1).

12. Method according to claim 11, wherein agents (A) and (B) contain the same oxidation dye precursors of the coupler type.

13. Method according to claim 11, wherein agents (A) and (B) contain different oxidation dye precursors of the coupler type.

14. Method according to claim 1, wherein the quantity ratio of the total quantity of all oxidation dye precursors of the coupler type (a2) in agent (A) to the total quantity of all oxidation dye precursors (b1) in agent (B) has a value (a2)/(b1) of 1:1 to 1:10.

15. Method according to claim 1, wherein agents (A) and (B) are allowed to act for a period of 5 to 30 minutes in step D).

16. Method according to claim 1, wherein agent (A) has a higher pH than does agent (B).

* * * * *